(12) United States Patent
Saxonov et al.

(10) Patent No.: US 8,951,939 B2
(45) Date of Patent: Feb. 10, 2015

(54) DIGITAL ASSAYS WITH MULTIPLEXED DETECTION OF TWO OR MORE TARGETS IN THE SAME OPTICAL CHANNEL

(75) Inventors: Serge Saxonov, Oakland, CA (US); Simant Dube, Pleasanton, CA (US); John Frederick Regan, San Mateo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 43 days.

(21) Appl. No.: 13/548,062

(22) Filed: Jul. 12, 2012

(65) Prior Publication Data

US 2013/0040841 A1 Feb. 14, 2013

Related U.S. Application Data

(60) Provisional application No. 61/507,082, filed on Jul. 12, 2011, provisional application No. 61/510,013, filed on Jul. 20, 2011.

(51) Int. Cl.
C40B 30/04 (2006.01)
C12Q 1/68 (2006.01)

(52) U.S. Cl.
CPC ............................ *C12Q 1/6851* (2013.01)
USPC ..................................................... 506/9

(58) Field of Classification Search
None
See application file for complete search history.

(56) References Cited

U.S. PATENT DOCUMENTS

| | | | |
|---|---|---|---|
| 3,575,220 A | 4/1971 | Davis et al. |
| 4,051,025 A | 9/1977 | Ito |
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |

(Continued)

FOREIGN PATENT DOCUMENTS

EP 1 522 582 A2 4/2005
EP 1 522 582 B1 4/2007

(Continued)

OTHER PUBLICATIONS

Qin et al, Nucleic Acid Research, 2008, vol. 36, No. 18, e116, pp. 1-8.*

(Continued)

*Primary Examiner* — Jennifer McDonald
*Assistant Examiner* — Valerie Toodle
(74) *Attorney, Agent, or Firm* — Kolisch Hartwell, P.C.

(57) ABSTRACT

System, including methods and apparatus, for performing a digital assay with multiplexed detection of two or more distinct targets in the same optical channel.

15 Claims, 5 Drawing Sheets

(56) References Cited

U.S. PATENT DOCUMENTS

| | | |
|---|---|---|
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |

(56) References Cited

U.S. PATENT DOCUMENTS

| | | |
|---|---|---|
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1* | 12/2009 | Pollack et al. .............. 435/6 |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0233686 A1* | 9/2010 | Higuchi et al. .............. 435/6 |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| GB | 1 503 163 | 3/1978 |
| GB | 2 097 692 | 11/1982 |
| JP | 0295433 | 4/1990 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2010/036352 A1 | 4/2010 |
| WO | 2011/034621 | 3/2011 |
| WO | 2011/079176 | 6/2011 |

OTHER PUBLICATIONS

Markey et al., Methods, 50 (2010), pp. 277-281.*
Qun Zhong et al., "Multiplex digital PCR: breaking the one target per color barrier of quantitative PCR", The Royal Society of Chemistry 2011, Lab Chip, 2011, vol. 11, pp. 2167-2174.
Simant Dube et al., "Mathematical Analysis of Copy Number Variation in a DNA Sample Using Digital PCR on a Nanofluidic Device", PLoS One, Aug. 6, 2008, vol. 3, Issue 8, e2876 pp. 1-9.
J. Smid-Korbar et al., "Efficiency and usability of silicone surfactants in emulsions," International Journal of Cosmetic Science 12, pp. 135-139, (1990), presented at the 15th IFSCC International Congress, Sep. 26-29, 1988, London.
A. Chittofrati et al., "Perfluoropolyether microemulsions," Progress in Colloid & Polymer Science 79, pp. 218-225, (1989).
Steven A. Snow, "Synthesis and Characterization of Zwitterionic Silicone Sulfobetaine Surfactants," Langmuir, vol. 6, No. 2, American Chemical Society, pp. 385-391, (1990).
Polydimethylsiloxane, 5 pgs., published in FNP 52 (1992).
Russell Higuchi et al., "Kinetic PCR Analysis: Real-time Monitoring of DNA Amplification Reactions," Bio/Technology vol. II, pp. 1026-1030, Sep. 11, 1993.

(56) References Cited

OTHER PUBLICATIONS

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).
Y. Sela et al., "Newly designed polysiloxane-graft-poly (oxyethylene) copolymeric surfactants: preparation, surface activity and emulsification properties," Colloid & Polymer Science 272, pp. 684-691, (1994).
M. Gasperlin et al., "The structure elucidation of semisolid w/o emulsion systems containing silicone surfactant," International Journal of Pharmaceutics 107, pp. 51-56, (1994).
Mieczyslaw A. Piatyszek et al., "Detection of telomerase activity in human cells and tumors by a telomeric repeat amplification protocol (TRAP)," Methods in Cell Science 17, pp. 1-15, (1995).
Anthony P. Shuber et al., "A Simplified Procedure for Developing Multiplex PCRs," Genome Research, published by Cold Spring Harbor Laboratory Press, pp. 488-493, (1995).
A. V. Yazdi et al., "Highly Carbon Dioxide Soluble Surfactants, Dispersants and Chelating Agents," Fluid Phase Equilibria, vol. 117, pp. 297-303, (1996).
Ariel A. Avilion et al., "Human Telomerase RNA and Telomerase Activity in Immortal Cell Lines and Tumor Tissues," Cancer Research 56, pp. 645-650, Feb. 1, 1996.
Shuming Nie et al., "Optical Detection of Single Molecules," Annu. Rev. Biophys. BiomoL Struct. vol. 26, pp. 567-596, (1997).
Edith J. Singley et al., "Phase behavior and emulsion formation of novel fluoroether amphiphiles in carbon dioxide," Fluid Phase Equilibria 128, pp. 199-219, (1997).
Olga Kalinina et al., "Nanoliter scale PCR with TaqMan Detection," Nucleic Acids Research, vol. 25, No. 10 pp. 1999-2004, (1997).
Zhen Guo et al., "Enhanced discrimination of single nucleotide polymorphisms by artificial mismatch hybridization," Nature Biotechnology vol. 15, pp. 331-335, Apr. 1997.
E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.
Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.
Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.
Bert Vogelstein et al., "Digital PCR," Proc. Natl. Acad. Sci. USA, vol. 96, pp. 9236-9241, Aug. 1999.
Anthony J. O'Lenick, Jr., "Silicone Emulsions and Surfactants," Journal of Surfactants and Detergents, vol. 3, No. 3, Jul. 2000.
N. Garti et al., "Water Solubilization in Nonionic Microemulsions Stabilized by Grafted Siliconic Emulsifiers," Journal of Colloid and Interface Science vol. 233, pp. 286-294, (2001).
Shinji Katsura et al., "Indirect micromanipulation of single molecules in water-in-oil emulsion," Electrophoresis, vol. 22, pp. 289-293, (2001).
Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).
Hidenori Nagai et al., "Development of a Microchamber Array for Picoliter PCR," Analytical Chemistry, vol. 73, No. 5, pp. 1043-1047, Mar. 1, 2001.
Christopher B. Price, "Regular Review Point of Care Testing," BMJ, vol. 322, May 26, 2001.
3M Specialty Materials, "3M Fluorinert Electronic Liquid FC-3283," product information guide, issued Aug. 2001.
Ivonne Schneegaβ et al., "Miniaturized flow-through PCR with different template types in a silicon chip thermocycler," Lab on a Chip, vol. 1, pp. 42-49, (2001).
Randla M. Hill, "Silicone surfactants—new developments," Current Opinion in Colloid & Interface Science 7, pp. 255-261, (2002).
Richard M. Cawthon, "Telomere measurement by quantitative PCR," Nucleic Acids Research, vol. 30, No. 10, pp. 1-6, (2002).
Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).
Shelley L. Anna et al., "Formation of dispersions using "flow focusing" in microchannels," Applied Physics Letters, vol. 82, No. 3, Jan. 20, 2003.
Goldschmidt GmbH, "Abil® EM 90 Emulsifier for the formulation of cosmetic W/O creams and lotions," degussa. creating essentials brochure, pp. 1-7, May 2003.
Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).
R. G. Rutledge et al., "Mathematics of quantitative kinetic PCR and the application of standard curves," Nucleic Acids Research, vol. 31, No. 16, pp. 1-6, (2003).
Chunming Ding et al., "Direct molecular haplotyping of long-range genomic DNA with M1-PCR," PNAS, vol. 100, No. 13, pp. 7449-7453, Jun. 24, 2003.
Devin Dressman et al., "Transforming single DNA molecules into fluorescent magnetic particles for detection and enumeration of genetic variations," PNAS, vol. 100, No. 15, Jul. 22, 2003.
Ulf Landegren et al., "Padlock and proximity probes for in situ and array-based analyses: tools for the post-genomic era," Comp. Funct. Genom, vol. 4, pp. 525-530, (2003).
Gudrun Pohl et al., "Principle and applications of digital PCR" review, www.future-drugs.com, Expert Rev. Mol. Diagn. 4(1), pp. 41-47, (2004).
Groff M. Schroeder et al., "Introduction to Flow Cytometry" version 5.1, 182 pgs. (2004).
Stéphane Swillens et al., "Instant evaluation of the absolute initial number of cDNA copies from a single real-time PCR curve," Nucleic Acids Research, vol. 32, No. 6, pp. 1-6, (2004).
Mats Gullberg et al., "Cytokine detection by antibody-based proximity ligation," PNAS, vol. 101, No. 22, pp. 8420-8424, Jun. 1, 2004.
Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
R. G. Rutledge, "Sigmoidal curve-fitting redefines quantitative realtime PCR with the prospective of developing automated high-throughput applications," Nucleic Acids Research. vol. 32, No. 22, pp. 1-8, (2004).
L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Anna Musyanovych et al., "Miniemulsion Droplets as Single Molecule Nanoreactors for Polymerase Chain Reaction," Biomacromolecules, vol. 6, No. 4, pp. 1824-1828, (2005).
Max Chabert et al., "Droplet fusion by alternating current (AC) field electrocoalescence in microchannels," Electrophoresis, vol. 26, pp. 3706-3715, (2005).
Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).

(56) References Cited

OTHER PUBLICATIONS

Marcel Margulies et al., "Genome sequencing in microfabricated high-density picolitre reactors," Nature, vol. 437, 51 pgs., Sep. 15, 2005.
Kristofer J. Thurecht et al., "Investigation of spontaneous microemulsion formation in supercritical carbon dioxide using high-pressure NMR," Journal of Supercritical Fluids, vol. 38, pp. 111-118, (2006).
Toshko Zhelev et al., "Heat Integration in Micro-Fluidic Devices," 16$^{th}$ European Symposium on Computer Aided Process Engineering and 9$^{th}$ International Symposium on Process Systems Engineering, pp. 1863-1868 published by Elsevier B.V. (2006).
Piotr Garstecki et al., "Formation of droplets and bubbles in a microfluidic T-junction—scaling and mechanism of break-up," Lab on a Chip, vol. 6, pp. 437-446, (2006).
Darren R. Link et al., "Electric Control of Droplets in Microfluidic Devices," Angewandte Chemie Int. Ed., vol. 45, pp. 2556-2560, (2006).
Peter Fielden et al., "Micro-Droplet Technology for High Throughout Systems and Methods," 1 pg., Mar. 8, 2006.
David Emerson et al., "Microfluidic Modelling Activities at C3M," Centre for Microfluidics & Microsystems Modelling, Daresbury Laboratory, pp. 1-26, May 15, 2006.
Richard Williams et al., "Amplification of complex gene libraries by emulsion PCR," Nature Methods, vol. 3, No. 7, pp. 545-550, Jul. 2006.
John H. Leamon et al., "Overview: methods and applications for droplet compartmentalization of biology," Nature Methods, vol. 3, No. 7, pp. 541-543, Jul. 2006.
Andrew D. Griffiths et al., "Miniaturising the laboratory in emulsion droplets," Trends in Biotechnology, vol. 24, No. 9, pp. 395-402, Jul. 14, 2006.
Jian-Bing Fan et al., "Highly parallel genomic assays," Nature Reviews/Genetics, vol. 7, pp. 632-644, Aug. 2006.
Jonas Jarvius et al., "Digital quantification using amplified single-molecule detection," Nature Methods, vol. 3, No. 9, pp. 15 pgs, Sep. 2006.
Kan Liu et al., "Droplet-based synthetic method using microflow focusing and droplet fusion," Microfluid Nanfluid, vol. 3, pp. 239-243, (2007), published online Sep. 22, 2006.
Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.
Kristofer J. Thurecht et al., "Kinetics of Enzymatic Ring-Opening Polymerization of ∈-Caprolactone in Supercritical Carbon Dioxide," Macromolecules, vol. 39, pp. 7967-7972, (2006).
Machiko Hori et al., "Uniform amplification of multiple DNAs by emulsion PCR," Biochemical and Biophysical Research Communications, vol. 352, pp. 323-328, (2007).
Frank Diehl et al., "Digital quantification of mutant DNA in cancer patients," Current Opinion in Oncology, vol. 19, pp. 36-42, (2007).
Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).
S. Mohr et al., "Numerical and experimental study of a droplet-based PCR chip," Microfluid Nanofluid, vol. 3, pp. 611-621, (2007).
Sigrun M. Gustafsdottir et al., "In vitro analysis of DNA-protein interactions by proximity ligation," PNAS, vol. 104, No. 9, pp. 3067-3072, Feb. 27, 2007.
Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Charles N. Baroud et al., "Thermocapillary valve for droplet production and sorting," Physical Review E 75, 046302, pp. 046302-1-046302-5, Apr. 5, 2007.
Qinyu Ge et al., "Emulsion PCR-based method to detect Y chromosome microdeletions," Analytical Biochemistry, vol. 367, pp. 173-178, May 10, 2007.

Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.
Y. M. Dennis Lo et al., "Digital PCR for the molecular detection of fetal chromosomal aneuploidy," PNAS, vol. 104, No. 32, pp. 13116-13121, Aug. 7, 2007.
Dayong Jin et al., "Practical Time-Gated Luminescence Flow Cytometry. II: Experimental Evaluation Using UV LED Excitation," Cytometry Part A • 71A, pp. 797-808, Aug. 24, 2007.
Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Nathan Blow, "PCR's next frontier," Nature Methods, vol. 4, No. 10, pp. 869-875, Oct. 2007.
Nicole Pamme, "continuous flow separations in microfluidic devices," Lab on a Chip, vol. 7, pp. 1644-1659, Nov. 2, 2007.
N. Reginald Beer et al., "On-Chip, Real-Time, Single-Copy Polymerase Chain Reaction in Picoliter Droplets," Analytical Chemistry, vol. 79, No. 22, pp. 8471-8475, Nov. 15, 2007.
Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Sigma-Aldrich, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.
Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hsin Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Vivienne N. Luk et al., "Pluronic Additives: A Solution to Sticky Problems in Digital Microfluidics," Langmuir, vol. 24, No. 12, pp. 6382-6289, May 16, 2008.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.

(56) References Cited

OTHER PUBLICATIONS

David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants—A Review," Silicone Spectator, Silitech LLC, May 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Yoon Sung Nam et al., "Nanosized Emulsions Stabilized by Semisolid Polymer Interphase," Langmuir, ACS Publications, Jul. 23, 2010.
Tatjana Schutze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
Thinxxs Microtechnology AG, "Emerald Biosystems: Protein Crystallization," 1 pg., downloaded Mar. 8, 2011.
Jiaqi Huang et al., "Rapid Screening of Complex DNA Samples by Single-Molecule Amplification and Sequencing," PLoS One, vol. 6, Issue 5, pp. 1-4, May 2011.
Burcu Kekevi et al., Synthesis and Characterization of Silicone-Based Surfactants as Anti-Foaming Agents, J. Surfact Deterg (2012), vol. 15, pp. 73-81, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
Labsmith, "Microfluid Components" webpage, downloaded Jul. 11, 2012.
Labsmith, "CapTite™ Microfluidic Interconnects" webpage, downloaded Jul. 11, 2012.
Nathan A. Tanner et al., "Simultaneous multiple target detection in real-time loop-mediated isothermal amplification," BioTechniques, vol. 53, pp. 8-19, Aug. 2012.
A. Scherer, California Institute of Technology, "Polymerase Chain Reactors" PowerPoint presentation, 24 pgs., date unknown.
Eschenback Optik GmbH, Optics for Concentrated Photovoltaics (CPV), 1 pg., date unknown.

\* cited by examiner

DIGITAL ASSAYS WITH MULTIPLEXED DETECTION OF TWO OR MORE TARGETS IN THE SAME OPTICAL CHANNEL

CROSS-REFERENCES TO PRIORITY APPLICATIONS

This application is based upon and claims the benefit under 35 U.S.C. §119(e) of U.S. Provisional Patent Application Ser. No. 61/507,082, filed Jul. 12, 2011; and U.S. Provisional Patent Application Ser. No. 61/510,013, filed Jul. 20, 2011. Each of these priority applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. patent application Ser. No. 13/251,016, filed Sep. 30, 2011; U.S. patent application Ser. No. 13/341,678, filed Dec. 30, 2011; U.S. patent application Ser. No. 13/424,304, filed Mar. 19, 2012; and Joseph R. Lakowicz, PRINCIPLES OF FLUORESCENCE SPECTROSCOPY ($2^{nd}$ Ed. 1999).

INTRODUCTION

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or the negative fraction then may be utilized in a Poisson equation to determine the concentration of the analyte in the partitions.

Digital assays frequently rely on amplification of a nucleic acid target in partitions to enable detection of a single copy of an analyte. Amplification may be conducted via the polymerase chain reaction (PCR), to achieve a digital PCR assay. The target amplified may be the analyte itself or a surrogate for the analyte generated before or after formation of the partitions. Amplification of the target can be detected optically from a fluorescent probe included in the reaction. In particular, the probe can include a dye that provides a fluorescence signal indicating whether or not the target has been amplified.

A digital PCR assay can be multiplexed to permit detection of two or more different targets within each partition. Amplification of the targets can be distinguished by utilizing target-specific probes labeled with different dyes. If a detector for a digital PCR assay can distinguishably measure the fluorescence emitted by N different dyes, then the assay is effectively capable of measuring N different targets. However, instruments with more optical channels, to detect emission from more dyes, are more expensive than those with fewer channels. Also, increasing the number of distinguishable dyes is expensive and becomes impractical beyond a certain number. On the other hand, many applications, especially where sample is limited, could benefit greatly from higher degrees of multiplexing.

A new approach is needed to increase the multiplex levels of digital assays.

SUMMARY

The present disclosure provides a system, including methods and apparatus, for performing a digital assay with multiplexed detection of two or more distinct targets in the same optical channel.

BRIEF DESCRIPTION OF THE DRAWINGS

FIG. 8 shows FAM intensities (top panel; FIG. 8A) and VIC intensities (bottom panel.

DETAILED DESCRIPTION

The present disclosure provides a system, including methods and apparatus, for performing a digital assay on a potentially greater number of targets through multiplexed detection of signals from reporters for two or more distinct targets in a common or shared channel ("the same optical channel"). The reporters may include the same fluorophore, such as FAM or VIC, or different fluorophores with similar spectral characteristics, so that light from two or more reporters may be collected simultaneously in the same optical channel. The assays may be constructed so that data for each target are distinguishable, for example, by choosing assays for each target that have sufficiently distinct endpoints (or time courses). The contents of each sample or sample partition may then be determined: those with no targets, those with a first assay (assay1) target, those with a second assay (assay2) target, and those with both, in a two-target assay. The total number of droplets positive for each target (e.g., target 1 and target 2) can be estimated by taking into account the total number of droplets in each population. Concentrations for each target may be estimated based on the number of droplets positive for each target and the total number of droplets, for example, using Poisson statistics. Moreover, the relative numbers of different targets (including reference targets) may be estimated, allowing determination of copy number (CN), copy number variation (CNV), and the presence/abundance of single nucleotide polymorphisms (SNPs), among other quantities. Copy number represents the number of copies of a given target present in a genome (e.g., humans have a diploid genome with a copy number of two for most autosomal genes). Copy number variation is a structural variation in the genome, such as deletions, duplications, translocations, and/or inversions, which may be a major source of heritable genetic variation, including susceptibility to disease (or disease itself) and responsiveness to disease treatment.

The assays may be extended in various ways. In some embodiments, the assays may involve analysis of more than two targets in the same channel. For example, an assay for three targets may generate eight clusters or populations of data, separated by intensity. In the same or other embodiments, some targets may be analyzed in one channel (e.g., a FAM channel), and one or more other targets may be analyzed in one or more other channels (e.g., a VIC channel). Three targets, two in a first channel and one in a second channel, would again generate eight clusters or populations of data, but they would be separated in a two-dimensional intensity space and so in principle more easily resolvable.

Further aspects of the present disclosure are presented in the following sections: (I) system overview, and (II) examples.

I. System Oerview

This section provides an overview of exemplary methods and apparatus for performing digital assays, in accordance with aspects of the present disclosure.

Figure 1:
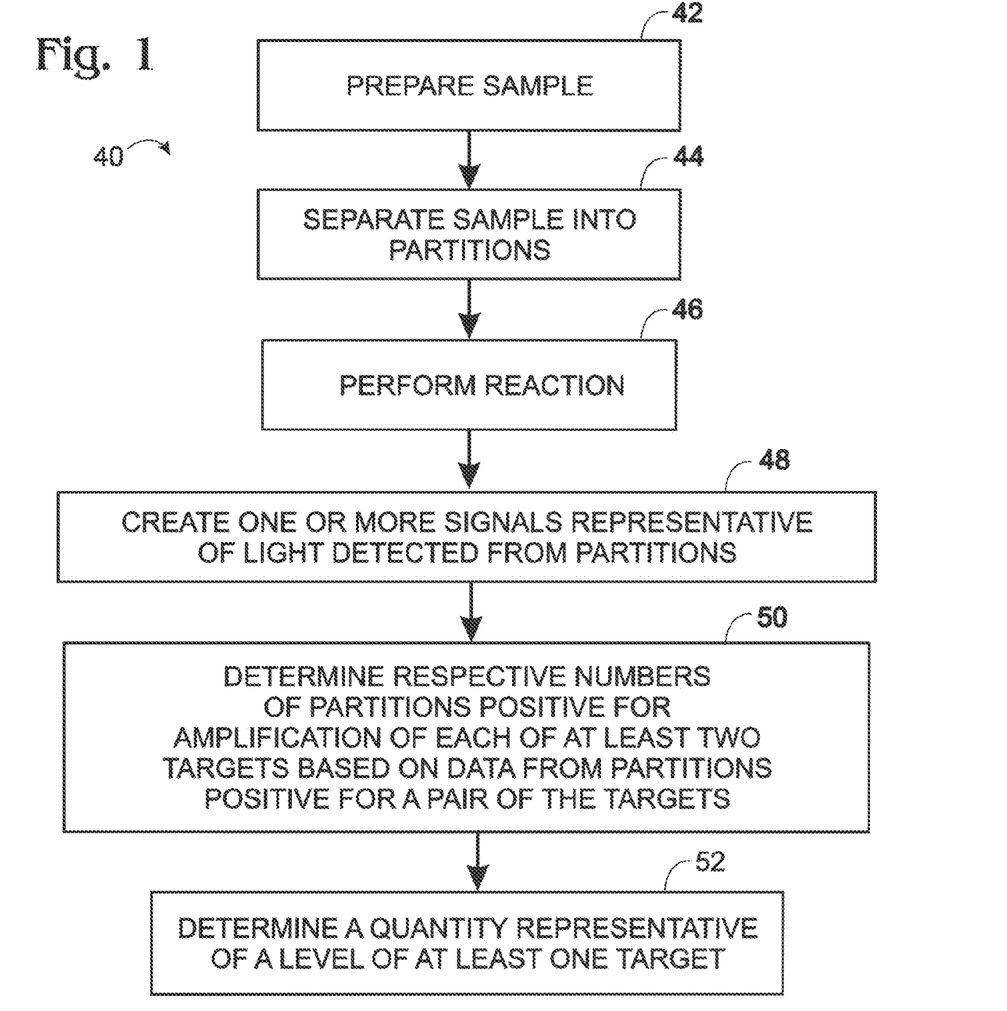
FIG. 1 is a flowchart of an exemplary method of performing a digital assay with multiplexed detection of two or more distinct targets in the same optical channel, in accordance with aspects of the present disclosure.

FIG. 1 shows a flowchart of an exemplary method 40 of performing a digital assay. The steps presented for method 40 may be performed in any suitable order and in any suitable combination. Furthermore, the steps may be combined with and/or modified by any other suitable steps, aspects, and/or features of the present disclosure.

Sample Preparation.

A sample may be prepared for the assay, indicated at 42. Preparation of the sample may include any suitable manipulation of the sample, such as collection, dilution, concentration, purification, lyophilization, freezing, extraction, combination with one or more assay reagents, performance of at least one preliminary reaction to prepare the sample for one or more reactions in the assay, or any combination thereof, among others. Preparation of the sample may include rendering the sample competent for subsequent performance of one or more reactions, such as one or more enzyme catalyzed reactions and/or binding reactions.

In some embodiments, preparation of the sample may include combining the sample with reagents for amplification and for reporting whether or not amplification occurred. Reagents for amplification may include any combination of primers for the targets, dNTPs and/or NTPs, at least one enzyme (e.g., a polymerase, a ligase, a reverse transcriptase, or a combination thereof, each of which may or may not be heat-stable), and/or the like. Accordingly, preparation of the sample may render the sample (or partitions thereof) capable of amplification of each of one or more targets, if present, in the sample (or a partition thereof). Reagents for reporting may include reporters for each target of interest. Accordingly, preparation of the sample for reporting may render the sample capable of reporting, or being analyzed for, whether or not amplification has occurred, on a target-by-target basis, and optionally the extent of any such amplification. The reporters each may be a labeled probe that includes a nucleic acid (e.g., an oligonucleotide) labeled with a luminophore, such as a fluorophore.

Sample Partitioning.

The sample may be separated into partitions, indicated at 44. Separation of the sample may involve distributing any suitable portion including up to all of the sample to the partitions. Each partition may be and/or include a fluid volume that is isolated from the fluid volumes of other partitions. The partitions may be isolated from one another by a fluid phase, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with a droplet generator, by agitation of the sample (e.g., shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 pL, among others.

The partitions, when formed, may be competent for performance of one or more reactions in the partitions. Alternatively, one or more reagents may be added to the partitions after they are formed to render them competent for reaction. The reagents may be added by any suitable mechanism, such as a fluid dispenser, fusion of droplets, or the like.

Sample Reactions.

One or more reactions may be performed in the partitions, indicated at 46. Each reaction performed may occur selectively (and/or substantially) in only a subset of the partitions, such as less than about one-half, one-fourth, or one-tenth of the partitions, among others. The reaction may involve a target, which may, for example, be a template and/or a reactant (e.g., a substrate), and/or a binding partner, in the reaction. The reaction may occur selectively (or selectively may not occur) in partitions containing at least one copy of the target.

The reaction may or may not be an enzyme-catalyzed reaction. In some examples, the reaction may be an amplification reaction, such as a polymerase chain reaction and/or ligase chain reaction. Accordingly, a plurality of amplification reactions for a plurality of targets may be performed simultaneously in the partitions.

Performing a reaction may include subjecting the partitions to one or more conditions that promote occurrence of the reaction. The conditions may include heating the partitions and/or incubating the partitions at a temperature above room temperature, such as at a denaturation temperature, an annealing temperature, and/or an extension temperature. In some examples, the conditions may include thermally cycling the partitions to promote a polymerase chain reaction and/or ligase chain reaction.

Signal Creation.

One or more signals may be created that are representative of light detected from the partitions, indicated at 48. The signal may represent an aspect of light, such as the intensity of the light, detected in the same optical channel from reporters for two or more distinct targets. The signals optionally may include data collected in one or more different channels (e.g., in different wavelength ranges (color regimes) from reporters for the same and/or different targets). The light detected from each reporter may be light emitted from a luminophore. The light detected in a given channel may be detected with the same sensor at the same time such that light detected from different reporters is summed or accumulated without attribution to a particular reporter. Thus, the signal may be a composite signal that represents two, three, four, or more reactions and thus two, three, four, or more targets of the reactions.

An optical channel represents a particular detection regime with which emitted light is generated and detected. The detection regime may be characterized by a wavelength or waveband (i.e., a wavelength regime) for detection of emitted light. If pulsed excitation light is used in the detection regime to induce light emission, the detection regime may be characterized by a wavelength or waveband for illumination with excitation light and/or a time interval during which light emission is detected with respect to each light pulse. Accordingly, optical channels that are different from each other may differ with respect to the wavelength/waveband of excitation light, with respect to the wavelength/waveband of emitted light that is detected, and/or with respect to the time interval during which emitted light is detected relative to each pulse of excitation light, among others.

The signal may be created based on detected light emitted from one or more reporters in the partitions. The one or more reporters may report whether at least one of two or more particular reactions represented by the signal has occurred in a partition and thus whether at least one copy of at least one of two or more particular targets corresponding to the two or more particular reactions is present in the partition. The strength of the signal corresponding to the reporters may be analyzed to determine whether or not at least one of the particular reactions has occurred and at least one copy of one of the particular targets is present. The strength may vary among the partitions according to whether at least one of the particular reactions occurred or did not occur (e.g., above a threshold and/or within a range) and at least one of the particular targets is present or absent in each partition.

Partitions may be analyzed and signals created at any suitable time(s). Exemplary times include at the end of an assay (endpoint assay), when reactions have run to completion and the data no longer are changing, or at some earlier time, as long as the data are sufficiently and reliably separated.

Number of Positives.

A number of partitions that are positive (or negative) for each target may be determined for the signal, indicated at 50. The signal detected from each partition, and the partition itself, may be classified as being positive or negative for each of the reactions/targets contributing to the signal. Classification may be based on the strength (and/or other suitable aspect) of the signal. If the signal/partition is classified as positive (+), for a given target, the reaction corresponding to that target is deemed to have occurred and at least one copy of the target is deemed to be present in the partition. In contrast, if the signal/partition is classified as negative (−), for a given target, the reaction corresponding to that target is deemed not to have occurred and no copy of the target is deemed to be present in the partition (i.e., the target is deemed to be absent from the partition). The data including all permutations of positives will generally fall into $2^N$ populations or clusters, where N is the number of targets, assuming that each population is distinguishable. Exemplary results for one, two, and three target systems in which data are collected in a single channel are shown in the following tables:

|  | Target A | Intensity |
| --- | --- | --- |
| Population 2 | + | Highest |
| Population 1 | − | Lowest |

|  | Target A | Target B | Intensity |
| --- | --- | --- | --- |
| Population 4 | + | + | Highest |
| Population 3 | + | − | Intermediate |
| Population 2 | − | + | Intermediate |
| Population 1 | − | − | Lowest |

| | Target A | Target B | Target C | Intensity |
|---|---|---|---|---|
| Population 8 | + | + | + | Highest |
| Population 7 | + | + | − | Intermediate |
| Population 6 | + | − | + | Intermediate |
| Population 5 | − | + | + | Intermediate |
| Population 4 | + | − | − | Intermediate |
| Population 3 | − | + | − | Intermediate |
| Population 2 | − | − | + | Intermediate |
| Population 1 | − | − | − | Lowest |

Target Level Determination.

A level of each target may be determined, indicated at 52. The level of each target may be determined based on the respective numbers of partitions positive for the target alone and for the target in combination with any other target(s). The calculation may be based on each target having a Poisson distribution among the droplets. The level may be a concentration. The levels may, for example, be estimated based on finding solutions to a series of linear equations. The total number of partitions may be counted or, in some cases, estimated. The partition data further may be used (e.g., directly and/or as concentration data) to estimate copy number (CN) and copy number variation (CNV), using any suitable algorithms such as those described elsewhere in the present disclosure.

Further aspects of sample preparation, droplet generation, signal detection, counting droplets, and target level determination, among others, that may be suitable for the system of the present disclosure are identified above in the Cross-References, which are incorporated herein by reference.

Figure 2:
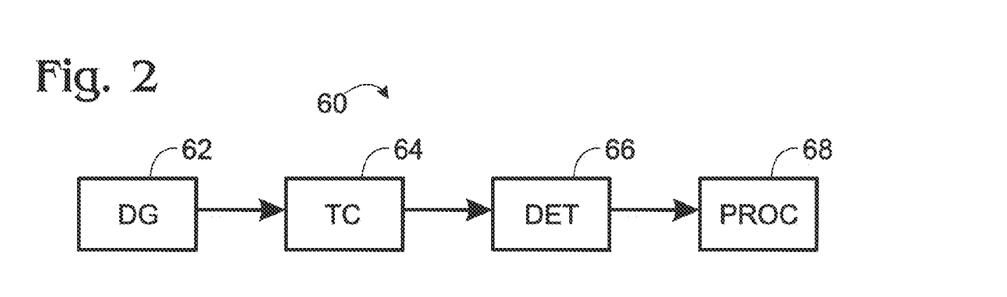
FIG. 2 is a schematic view of an exemplary apparatus for performing the digital assay of FIG. 1, in accordance with aspects of the present disclosure.

FIG. 2 shows an exemplary apparatus 60 for performing the digital assay of FIG. 1. Apparatus 60 may include a partitioning assembly, such as a droplet generator 62 ("DG"), a thermal incubation assembly, such as a thermocycler 64 ("TC"), a detection assembly (a detector) 66 ("DET"), and a data processing assembly (a processor) 68 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets) or signals/data, between the assemblies. Any suitable combination of the assemblies may be operatively connected to one another, and/or one or more of the assemblies may be unconnected to the other assemblies, such that, for example, material/data is transferred manually.

Apparatus 60 may operate as follows. Droplet generator 62 may form droplets disposed in a continuous phase. The droplets may be cycled thermally with thermocycler 64 to promote amplification of targets in the droplets. Signals may be detected from the droplets with detector 66. The signals may be processed by processor 68 to determine numbers of droplets and/or target levels, among others II. Examples This section presents selected aspects and embodiments of the present disclosure related to methods of performing digital assays with multiplexed detection of two or more targets in the same channel.

Example 1

Digital PCR Assays with Multiplexed Detection in the Same Channel

This example describes an exemplary digital PCR assay with multiplexed detection of two targets, using two probes, analyzed in the same channel. Other assays may involve three or more targets and three or more probes, where at least two targets are analyzed in the same channel.

Figure 3:
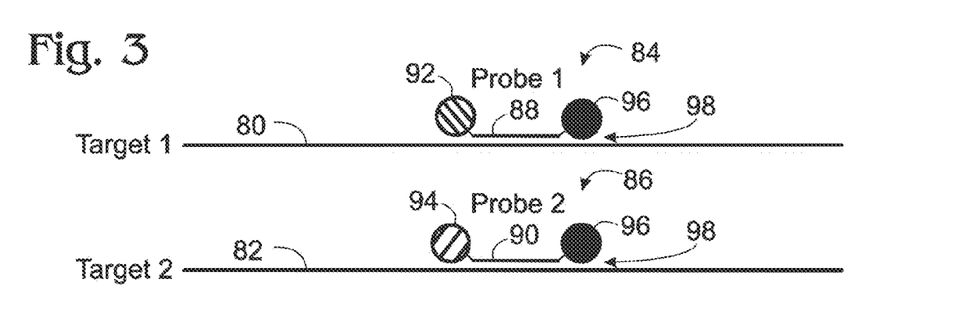
FIG. 3 is a schematic view of a pair of targets and corresponding probes capable of reporting the presence or absence of the targets via emitted light that may be detected together in the same channel for one or both targets in a digital PCR assay, in accordance with aspects of the present disclosure.

FIG. 3 shows a pair of targets 80, 82 ("Target 1" and "Target 2") and corresponding probes 84, 86 ("Probe 1" and "Probe 2") that may be used to create a dedicated signal for each target in a digital PCR assay. Each probe may include an oligonucleotide 88, 90, a fluorophore 92, 94, and a quencher 96. Each of the fluorophore and the quencher may (or may not) be conjugated to the oligonucleotide by a covalent bond. The probe also or alternatively may include a binding moiety (a minor groove binder) for the minor groove of a DNA duplex, which may be conjugated to the oligonucleotide and which may function to permit a shorter oligonucleotide to be used in the probe.

Each oligonucleotide may provide target specificity by hybridization predominantly or at least substantially exclusively to only one of the two targets. Hybridization of the oligonucleotide to its corresponding target is illustrated schematically at 98.

Fluorophores 92, 94, which may be the same or different, create detectable but distinguishable signals in the same channel, allowing multiplexing in that channel. The signals may be distinguishable because an aspect of the fluorescence is different for one fluorophore than for the other fluorophore(s). For example, the intensity associated with one fluorophore, following reaction, may be lower or higher than the intensity(ies) associated with the other fluorophore(s). In some embodiments, one probe may be labeled with a different number of fluorophores than the other probe, and/or the probes may be located in slightly different local environments, creating a different level of fluorescence for each probe following reaction. Alternatively, or in addition, both probes may be labeled with the same number of fluorophores (e.g., one fluorophore), but there may be more or less of one probe than the other in the sample, so that a greater or smaller signal is created when the reactions have occurred. In some cases, the fluorophores themselves might be different, with one more or less intrinsically fluorescent than the other (e.g., due to differences in extinction coefficient, quantum yield, etc.), so long as each fluorophore can be detected in the same channel. Exemplary fluorophores that may be suitable include FAM, VIC, ROX, TAMRA, JOE, etc., among others.

Quencher 96 is configured to quench the signal produced by fluorophore 92 or 94 in a proximity-dependent fashion. Accordingly, light detected from the fluorophore may increase when the associated oligonucleotide 88 or 90 binds to the amplified target, to increase the separation between the fluorophore and the quencher, or when the probe is cleaved and the fluorophore and quencher become uncoupled during target amplification, among others. The quencher may be the same or different for each type of fluorophore. Here, the assay is designed so that the presence of a target gene leads to an increase in corresponding intensity, because amplification reduces quenching. In other assays, the reverse could be true, such that the presence of a target caused a decrease in corresponding intensity (although it typically is easier to detect a signal against a dark background than the opposite). Moreover, some embodiments may be constructed without a quencher, so long as the fluorescence and so the signal changes upon amplification.

Figure 4:
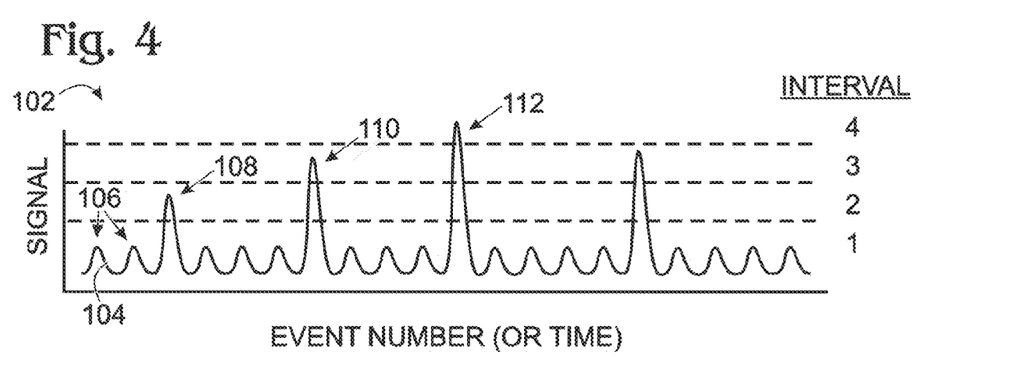
FIG. 4 is an exemplary graph showing a signal that may be created by detecting light emitted from the probes of FIG. 3 in a digital PCR assay performed in droplets, with the signal created by detecting light from each target together in the same channel from a fluid stream containing the droplets, in accordance with aspects of the present disclosure.

FIG. 4 shows an exemplary graph 102 of data corresponding to an exemplary digital PCR assay for Target 1 and Target 2 performed in droplets. The graph plots a signal 104 that represents light detected from probes 84, 86 (and/or one or more modified (e.g., cleavage) products thereof) (see FIG. 3).

The signal is created from light detected over time in a single channel from a fluid stream containing the droplets and flowing through an examination region of the channel. The signal may be analyzed to determine whether neither Target, Target 1 alone, Target 2 alone, or both Targets 1 and 2 are present in each droplet. In particular, the strength or intensity of the signal in a system with two targets may be divided or thresholded into four intervals corresponding to no Target (Interval 1), Target 1 alone (Interval 2), Target 2 alone (Interval 3), or both Targets 1 and 2 (Interval 4):

Peaks 106 with maxima in Interval 1 correspond to droplets containing no Target (T1−/T2−). The measured signal corresponds to background (e.g., background fluorescence, scattering, etc.) and does not reflect the presence or amplification of either Target.

Peaks 108 with maxima in Interval 2 correspond to droplets containing Target 1 but not containing Target 2 (T1+/T2−). The measured signal corresponds to signal from Target 1 plus background and reflects amplification of Target 1 implying the presence of Target 1.

Peaks 110 with maxima in Interval 3 correspond to droplets containing Target 2 but not containing Target 1 (T1−/T2+). The measured signal corresponds to signal from Target 2 plus background and reflects amplification of Target 2 implying the presence of Target 2.

Peaks 112 with maxima in Interval 4 correspond to droplets containing both Targets 1 and 2 (T1+/T2+). The measured signal corresponds to signal from both Targets 1 and 2 plus background and reflects amplification of Targets 1 and 2 implying the presence of Targets 1 and 2.

In the present example, each droplet, whether positive or negative for each target, produces an increase in signal strength above the baseline signal that forms an identifiable peak 106, 108, 110, 112. Accordingly, the signal may vary in strength with the presence or absence of a droplet and with the presence or absence of a corresponding target.

The assignment of a droplet to a particular outcome (i.e., to one of T1−/T2−, T1+/T2−, T1−/T2+, and T1+/T2+) may be performed using any suitable algorithm. In the example above, peak heights (i.e., intensity values) associated with each outcome are sufficiently different that each can be unambiguously identified and assigned. Specifically, the peaks are assigned based on intervals delineated by values lying between (e.g., half way between) the peak heights for one outcome and the peak heights for adjacent outcomes. In other cases, the peak heights for each outcome may overlap at their extremes, so that thresholding may be neither simple nor linear. In such cases, statistical methods such as expectation maximization algorithms may be used to estimate the number of droplets or peaks associated with each outcome and the associated concentrations.

Example 2

Digital PCR Assay to Assess Copy Number of C61

Figure 5:
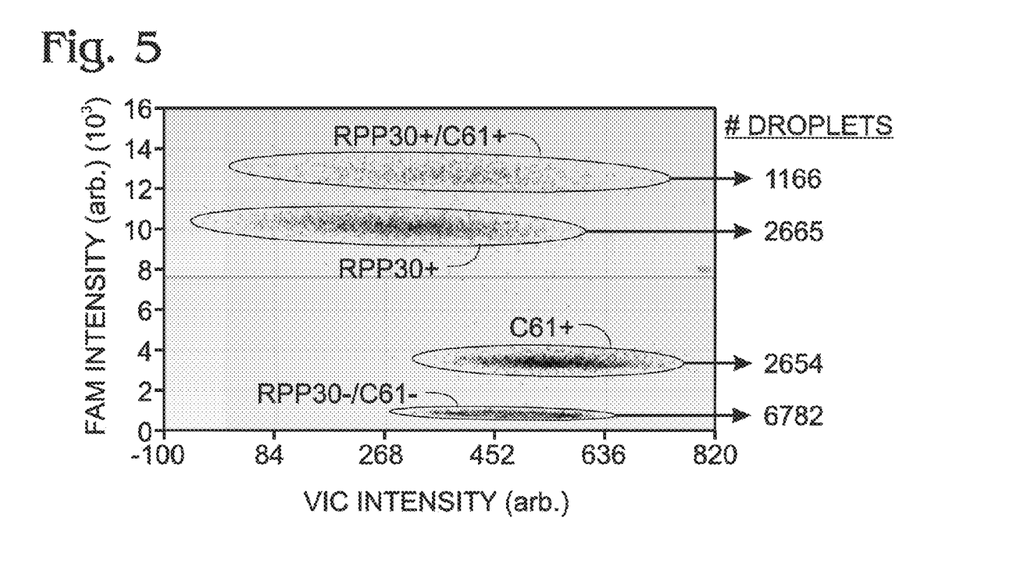
FIG. 5 is an exemplary graph showing droplet (or peak) intensities in arbitrary units ("arb.") for a C61/RPP30 droplet assay, where data from reporters for C61 and RPP30 are collected together in the same optical channel and plotted as a function of intensity in a FAM channel (vertical axis) versus intensity in a VIC channel (horizontal axis).
Figure 6:
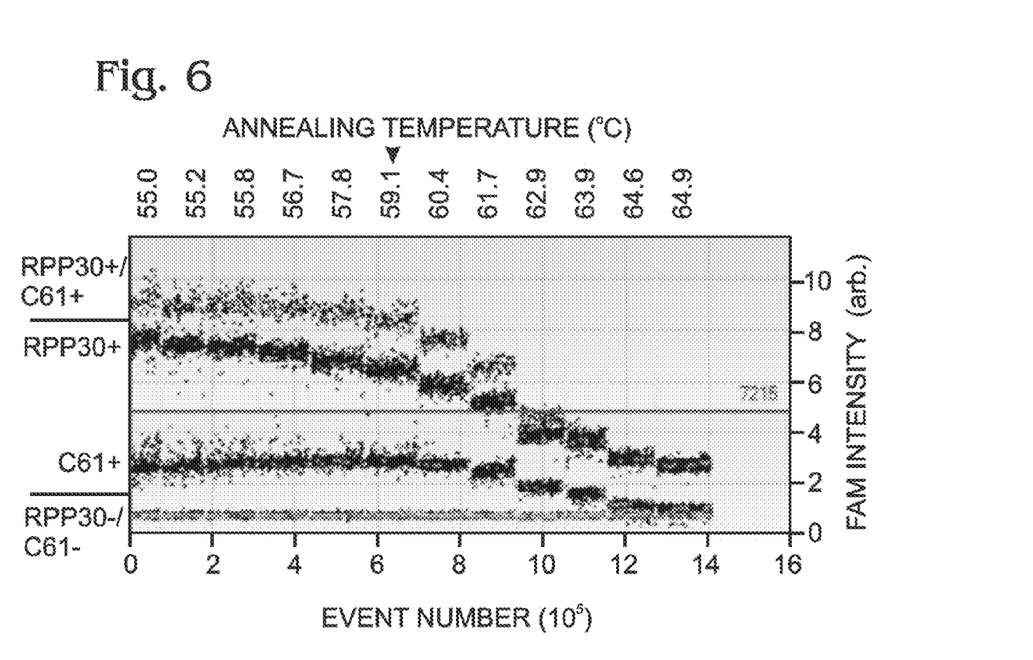
FIG. 6 is a graph showing FAM intensities for the C61/RPP30 droplet assay of FIG. 5 for twelve different sets of assay conditions, namely, amplification of the C61 and RPP30 targets with different annealing temperatures (given in Celsius and denoted, from left to right, 55.0, 55.2, ..., 64.6, and 64.9).

This example describes a first exemplary digital PCR assay, in which multiplexing in a single channel is used to assess copy number of the C61 gene; see FIGS. 5 and 6. Specifically, signals from two probes, one for the gene of interest, C61, and one for a reference gene, RPP30, are collected together, as a single signal, in a single channel and used to assess the number of copies of the gene of interest relative to the number of copies of the reference gene.

The principles described here may be used with any suitable gene(s). In this example, C61 is a gene of interest, for which information on copy number is sought, and RPP30 is a reference gene, which codes for ribonuclease P protein subunit p30, that is known to have two copies per genome.

The principles described here also may be extended to additional genes of interest, for example, two or three or more genes of interest, and may or may not involve reference genes such as RPP30. The number of copies may be determined absolutely, if the copy number of at least one of the genes (e.g., the reference gene) is known, or relatively, if the copy number of none of the genes is known.

FIG. 5 is a graph showing data for the exemplary C61/RPP30 system. Specifically, FIG. 5 shows intensity in the FAM channel plotted as a function of intensity in the VIC channel for each droplet in a digital PCR assay. Visually, the data comprise four distinct populations, corresponding to four distinct ranges of FAM intensity (the intensities in the VIC channel are all low and overlapping). The assay is constructed so that amplification of C61 leads to a lower FAM intensity than amplification of RPP30 (although it would work as well if the reverse were true). The four populations may be summarized as follows:

Population 1, with the lowest FAM intensity, corresponds to droplets that are negative for RPP30 and C61 (i.e., droplets that did not include either gene).

Population 2, with the lower of two intermediate FAM intensities, corresponds to droplets that are positive for C61 and negative for RPP30 (i.e., droplets that included the C61 gene but did not include the RPP30 gene).

Population 3, with the higher of two intermediate FAM intensities, corresponds to droplets that are positive to RPP30 and negative for C61 (i.e., droplets that included the RPP30 gene but did not include the C61 gene).

Population 4, with the highest FAM intensity, corresponds to droplets that are positive for RPP30 and C61 (i.e., droplets that included both genes).

The number of droplets in each population may be counted using any suitable mechanism(s), during or following data acquisition. Here, because the intensities are widely separated, the number may be counted by assigning suitable intensity ranges or intervals to each population, as in Example 1, so that droplets falling within a selected intensity range are designated as falling within the population corresponding to that range. The results of such counting are summarized in the following table:

|  | RPP30 | C61 | # Droplets |
| --- | --- | --- | --- |
| Population 4 | + | + | 1168 |
| Population 3 | + | − | 2865 |
| Population 2 | − | + | 2854 |
| Population 1 | − | − | 6782 |

Here, + means that the assay is positive for the indicated gene (i.e., that the indicated gene is present), and − means that the assay is negative for the indicated gene (i.e., that the indicated gene was absent). There are 4033 droplets containing RPP30 (i.e., that are positive for RPP30, irrespective of whether they are positive or negative for C61), as determined by adding the number of droplets in Populations 3 and 4 (i.e., by adding 2865 and 1168, respectively). There are 4022 droplets containing C61 (i.e., that are positive for C61, irrespective of whether they are positive or negative for RPP30), as determined by adding the number of droplets in Populations 2 and 4 (i.e., by adding 2854 and 1168, respectively). Thus, the ratio of C61 to RPP30 is 4022/4033=0.997=1:1 within experimental error. Thus, because RPP30 is known to have two copies per genome, C61 must also have two copies (i.e., the copy number of C61 is two).

FIG. 6 shows FAM intensities for the C61/RPP30 system of FIG. 5 for twelve different sets of droplets exposed to twelve different annealing temperatures (denoted, from left to right, 55.0, 55.2, . . . , 64.6, and 64.9) during thermal cycling to promote target amplification. The data show that there is sufficient resolution between the four populations to perform the assay in a single channel under a variety of experimental conditions. The data shown in FIG. 5 correspond to one of the conditions in this plot, namely, amplification with an annealing temperature of 59.1° C. (marked in FIG. 6 with an arrowhead).

The annealing temperature may be selected from among the various temperatures tested, based on comparison of collected intensity data. For example, the resolution or separation of each population of droplets from one another in the plot for the various annealing temperatures may be compared to permit selection of a suitable annealing temperature for further data collection and/or analysis. For example, here, the annealing temperature of 59.1° C. offers the best separation between each different population of droplets within the set. In particular, at this annealing temperature, data from double-positive droplets (RPP30+/C61+; the population of highest intensity) are well resolved from data for single-positive droplets (RPP30+ or C61+; the two populations of intermediate intensity), which in turn are well resolved from each other and from data for double-negative droplets (RPP30−/C61−; the population of lowest intensity).

The resolution provided by selection of an optimal annealing temperature may permit determination, for each target, a respective number of droplets that are positive for the target alone at the selected annealing temperature. Also, at least one number of droplets positive for more than one target may be determined. The total number of droplets positive for each target then may be determined based on the respective numbers and the at least one number.

In some cases, signal detection may be performed first on only a fraction of each set of droplets. Additional droplets from the particular set corresponding to the selected annealing temperature then may be run through the detector to provide additional data for analysis. In other cases, only a fraction of the data collected for each set of droplets may be plotted and/or compared, and then additional data collected for the particular set corresponding to the selected annealing temperature may be plotted and/or analyzed.

Example 3

Digital PCR Assay to Assess Copy Number of C63

Figure 7:
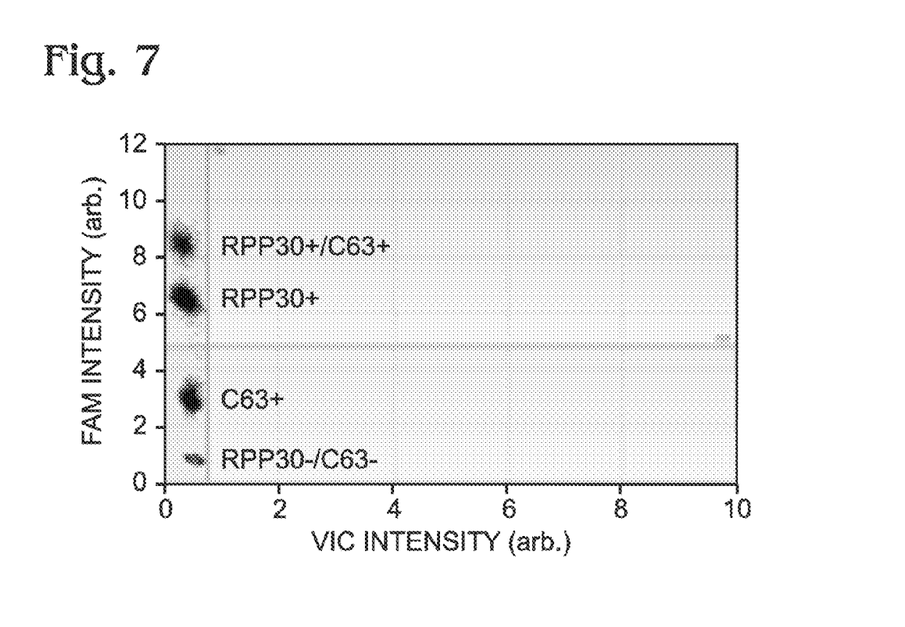
FIG. 7 is an exemplary graph showing droplet (or peak) intensities for a C63/RPP30 droplet assay, where data from reporters for C63 and RPP30 are collected and plotted as a function of intensity in a FAM channel (vertical axis) versus intensity in a VIC channel (horizontal axis).
Figure 8A:
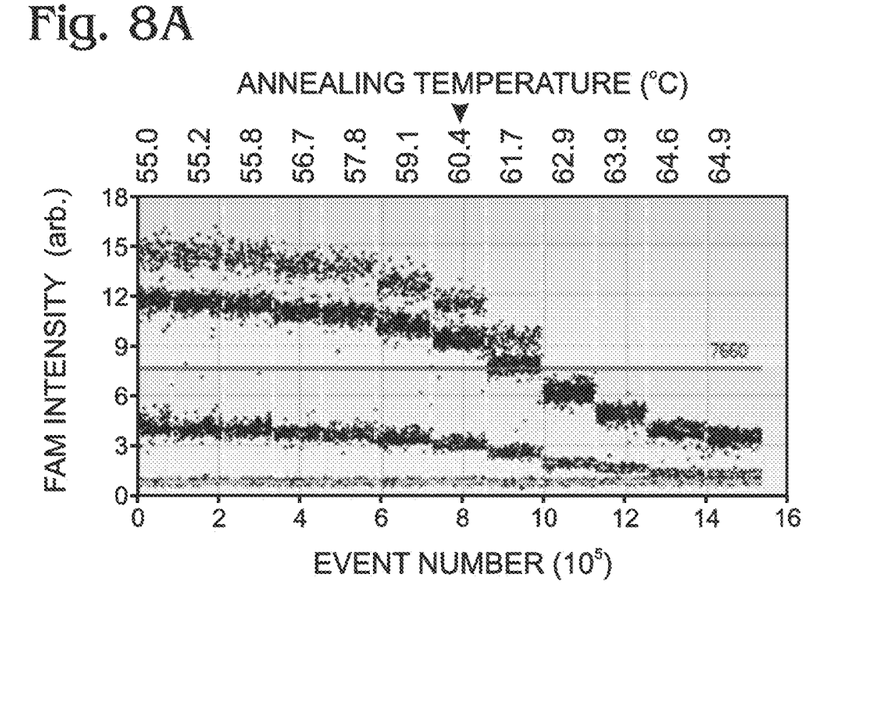
Figure 8B:
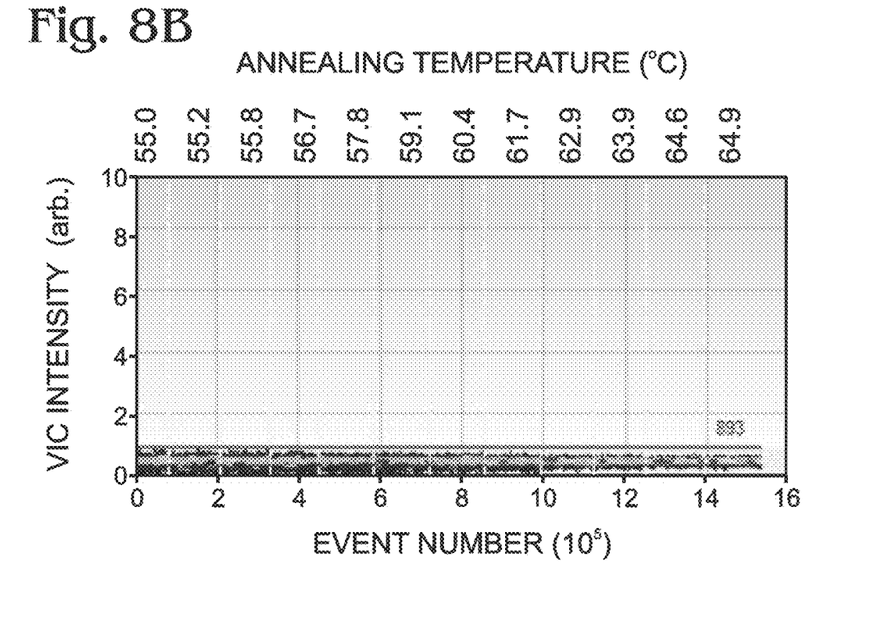
FIG. 8B) for the C63/RPP30 droplet assay of FIG. 7 for twelve different sets of assay conditions, namely, amplification of the C61 and RPP30 targets with different annealing temperatures (given in degrees Celsius and denoted, from left to right, 55.0, 55.2, . . . , 64.6, and 64.9).

This example describes a second exemplary digital PCR assay, in which multiplexing in a single channel is used to assess copy number of the C63 gene; see FIGS. 7 and 8. Specifically, signals from two probes, one for the gene of interest, C63, and one for a reference gene, again RPP30, are collected in a single channel and used to assess the number of copies of the gene of interest relative to the number of copies of the reference gene.

FIG. 7 is a graph showing data for the exemplary C63/RPP30 system. Like FIG. 5, FIG. 7 shows intensity in the FAM channel plotted as a function of intensity in the VIC channel for each droplet in a digital PCR assay. However, unlike FIG. 5, this system includes probes for RPP30 and C63 instead of RPP30 and C61. The data again show four distinct populations, corresponding in order of decreasing intensity in the FAM channel to RPP30+/C63+, RPP30+/C63−, RPP30−/C63+, and RPP30−/C63−. The number of droplets counted in each of these bins corresponds to 3552 RPP30 positive droplets, 3441 C63 positive droplets, and 6224 negative droplets. Thus, the ratio of C63 to RPP30 is 3441/3552=0.969=1:1 within experimental error. Thus, like C61, C63 must have two copies (i.e., the copy number of C63 is two).

FIG. 8A shows FAM intensities and FIG. 8B shows VIC intensities for the C63/RPP30 system of FIG. 7 for twelve different sets of experimental conditions (i.e., different annealing temperatures for amplification). The data show that there is sufficient resolution between the four populations to perform the assay in a single channel under a variety of experimental conditions. The data shown in FIG. 7 correspond to one of the conditions in these plots.

Example 4

Digital Assay with More Luminophores than Optical Channels

Figure 9:
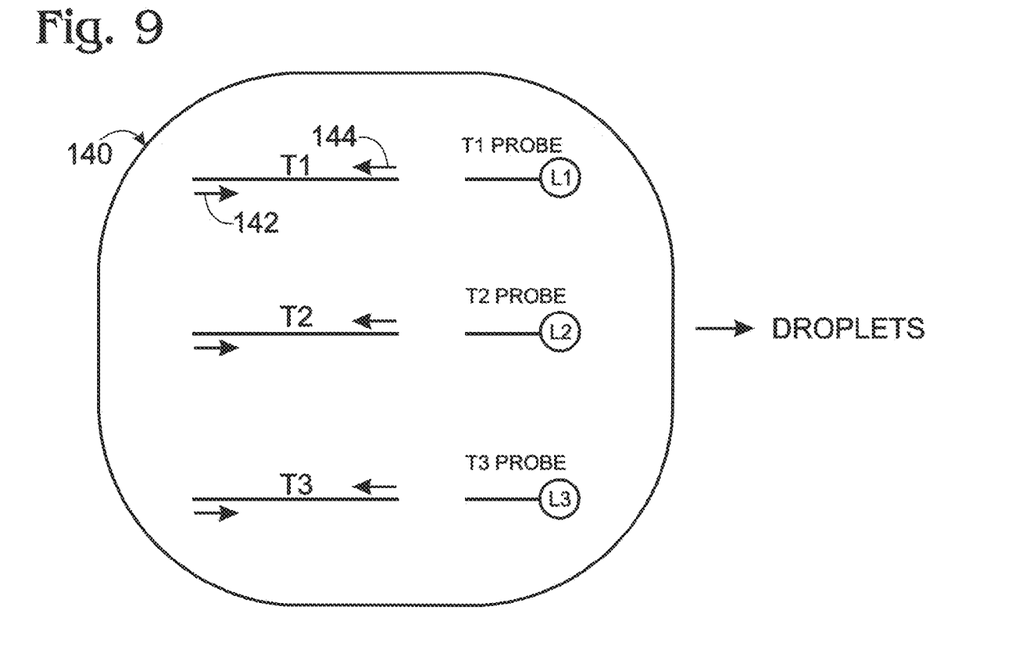
FIG. 9 is a schematic representation of an exemplary bulk phase mixture being separated into droplets during performance of an exemplary digital assay with multiplexed detection of three or more distinct targets (T1, T2, and T3) using a reporter for each target (a T1 probe, a T2 probe, and a T3 probe) each including a different luminophore (L1, L2, and L3, respectively), in accordance with aspects of the present disclosure.
Figure 10:
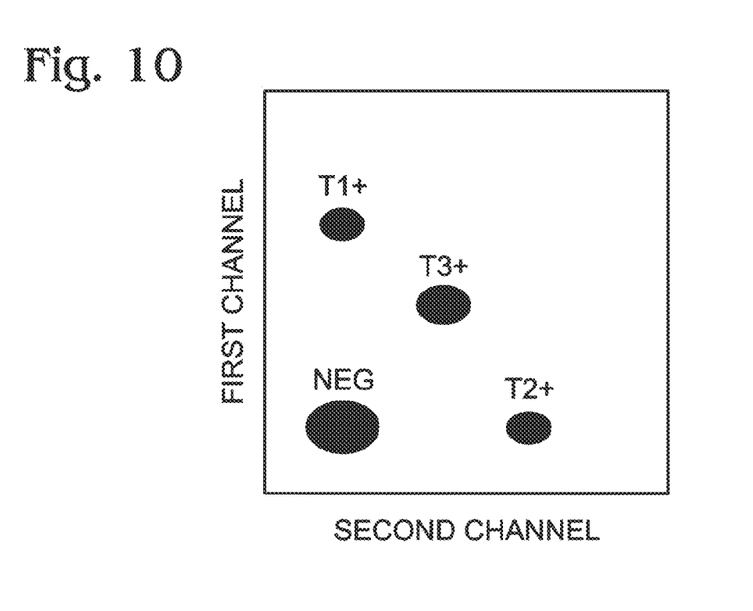
FIG. 10 is a schematic representation of an exemplary graph showing droplet (or peak) intensities for a T1/T2/T3 droplet assay that may be performed with the droplets of FIG. 9, where data from the T1, T2, and T3 probes are collected in a first optical channel and a second optical channel and plotted as a function of intensity in the first channel (vertical axis) versus intensity in the second channel (horizontal axis), with intensities produced by exemplary populations or clusters of negative (NEG), T1-positive (T1+), T2-positive (T2+), and T3-positive (T3+) droplets represented by filled ellipses, in accordance with aspects of the present disclosure.

This example describes an exemplary digital assay with multiplexed analysis of targets using more luminophores than the number of optical channels used for detecting signals from the luminophores; see FIGS. 9 and 10.

FIG. 9 shows an exemplary bulk phase mixture 140 being separated into droplets during performance of an exemplary digital assay with multiplexed detection of three or more distinct targets (e.g., identified here as T1, T2, and T3). Mixture 140 may include a forward primer 142 and a reverse primer 144 for each target. The mixture also may include a reporter for amplification of each target (such as a T1 probe, a T2 probe, and a T3 probe). Each reporter may be a probe including an oligonucleotide labeled with a different luminophore (namely, L1, L2, and L3, respectively). Accordingly, luminescence from the T1-T3 probes, and more particularly, the L1, L2, and L3 luminophores, may report whether or not target T1, T2, and T3, respectively, are present in each individual droplet.

FIG. 10 schematically represents an exemplary graph showing droplet (or peak) intensities for a T1/T2/T3 droplet assay that may be performed with the droplets of FIG. 9. Data from the T1, T2, and T3 probes are collected in a first optical channel and a second optical channel and plotted as a function of intensity in the first channel (vertical axis) versus intensity in second channel (horizontal axis). Intensities produced by exemplary populations or clusters of negative, T1-positive, T2-positive, and T3-positive droplets are identified by filled ellipses, with the size of each ellipse corresponding to the number of droplets in each population. To simplify the presentation, double-positive populations (T1+/T2+, T1+/T3+, and T2+/T3+) and the triple-positive population (T1+/T2+/T3+) are not shown.

Each luminophore may be at least predominantly or substantially exclusively detectable in only one optical channel, or may be substantially detectable in two or more optical channels. For example, L1 of the T1 probe is substantially detectable in the first channel but not the second channel, L2 of the T2 probe is substantially detectable in the second channel but not the first channel, and L3 of the T3 probe is substantially detectable in both channels. More generally, L3 may generate a distinguishable intensity and/or a different ratio of signal intensities for amplification of the T3 target in each channel relative to the intensity and/or ratio produced by L1 for amplification of the T1 target and produced by L2 for amplification of the T2 target. As a result, the population of T3-only positives is resolved from the T1-only and T2-only populations. Also, the populations containing more than one target may be resolved and distinguishable from one another and from the single-target populations and the negative population.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of performing a digital assay, comprising:
amplifying at least two distinct targets in droplets containing a reporter for each distinct target, wherein the reporters each are labeled with a same luminophore;
detecting a signal from the droplets representing combined emission of light in a same wavelength regime from the reporters for the distinct targets, wherein each reporter provides a portion of the signal having an intensity that varies according to whether or not the corresponding distinct target is present in a droplet, and wherein a plurality of the droplets each contain at least two of the distinct targets and have a distinguishable intensity of the signal relative to droplets containing only one of the distinct targets;
determining for each distinct target a number of droplets that are positive for only one of the distinct targets;
determining at least one number of droplets that are positive for at least two of the distinct targets; and
determining a quantity representative of a level of at least one of the distinct targets.

2. The method of claim 1, wherein the quantity representative of a level is a concentration of the at least one distinct target.

3. The method of claim 2, wherein the step of determining a quantity representative of a level further comprises a step of ascertaining a total number of droplets based on the signal, and obtaining a concentration of the at least one distinct target based on the total number of droplets.

4. The method of claim 1, wherein the quantity representative of a level is a copy number of the at least one distinct target in a sample disposed in the droplets.

5. The method of claim 1, wherein the step of determining a quantity representative of a level further comprises a step of obtaining a copy number of a first target by comparing the number of droplets positive for the first target with the number of droplets positive for a second target, the first and second targets being among the at least two distinct targets.

6. The method of claim 5, wherein the copy number of the second target is known, and wherein the copy number of the first target is determined by calculating the ratio of the number of droplets positive for the first target to the number of droplets positive for the second target and multiplying the ratio by the copy number of the second target.

7. The method of claim 5, wherein the copy number of the second target is unknown, and wherein the copy number of the first target is obtained relative to the copy number of the second target as the ratio of the number of droplets positive for the first target to the number of droplets positive for the second target.

8. The method of claim 1, wherein the luminophore is selected from the group consisting of FAM, VIC, ROX, TAMRA, and JOE.

9. The method of claim 1, wherein the at least two distinct targets include a first target and a second target, wherein the step of determining for each distinct target includes a step of counting a number of droplets positive for the first target and not the second target and a number of the droplets positive for the second target and not the first target, and wherein the step of determining at least one number of droplets includes a step of counting a number of droplets positive for both the first target and the second target.

10. The method of claim 1, the signal being a first signal, further comprising:
detecting from the droplets a second signal representing emission of light from an additional reporter for an additional target, the additional reporter providing at least a portion of a second signal having an intensity that varies according to whether or not the corresponding additional target is present in a droplet, wherein the first signal and second signal correspond to emission of light in different wavelength regimes;
counting a number of the droplets that are positive for the additional target based on the second signal; and
determining a quantity representative of a level of the additional target in the droplets.

11. The method of claim 10, wherein the first signal is collected from a first luminophore and the second signal is collected from a second luminophore.

12. The method of claim 1, wherein the droplets include a first probe reporting a presence or absence of a first target in individual droplets, a second probe reporting a presence or absence of a second target in individual droplets, and a third probe reporting a presence or absence of a third target in individual droplets, and wherein a signal from the first and second probes represents light emitted in a first wavelength regime and a signal from the third probe represents light emitted in a second wavelength regime distinct from the first wavelength regime.

13. The method of claim 1, wherein each reporter is a probe including an oligonucleotide, and wherein each of the distinct targets is a nucleic acid.

14. The method of claim 1, wherein the intensity of the signal detected from droplets positive for only a first target of the at least two distinct targets is distinguishable from the intensity of the signal detected from droplets positive for only a second target of the at least two distinct targets.

15. The method of claim 1, wherein the step of detecting a signal is performed with the droplets disposed in a fluid stream flowing through an examination region.

* * * * *